(12) United States Patent
Smith et al.

(10) Patent No.: US 8,992,653 B2
(45) Date of Patent: Mar. 31, 2015

(54) SEED TREATMENT METHODS AND COMPOSITIONS

(75) Inventors: R. Stewart Smith, Pewaukee, WI (US); Ahsan Habib, Roanoke, VA (US); John Kosanke, Waukesha, WI (US)

(73) Assignee: Novozymes Bioag A/S, Bagsvaerd (DK)

( * ) Notice: Subject to any disclaimer, the term of this patent is extended or adjusted under 35 U.S.C. 154(b) by 88 days.

(21) Appl. No.: 13/608,662

(22) Filed: Sep. 10, 2012

(65) Prior Publication Data

US 2013/0061645 A1    Mar. 14, 2013

Related U.S. Application Data

(60) Provisional application No. 61/532,234, filed on Sep. 8, 2011, provisional application No. 61/568,435, filed on Dec. 8, 2011.

(51) Int. Cl.
*C05F 11/08* (2006.01)
*A01N 25/00* (2006.01)
*A01N 43/16* (2006.01)

(52) U.S. Cl.
CPC .................................. *A01N 43/16* (2013.01)
USPC ............................................. 71/6; 71/64.07

(58) Field of Classification Search
CPC .................................................... A01N 43/16
USPC ..................... 504/100; 71/6, 11, 64.01, 64.13
See application file for complete search history.

(56) References Cited

U.S. PATENT DOCUMENTS

| | | | |
|---|---|---|---|
| 4,536,207 A | 8/1985 | McCandliss | |
| 4,804,750 A | 2/1989 | Nishimura | |
| 4,812,159 A | 3/1989 | Freepons | |
| 4,886,541 A | 12/1989 | Hadwiger | |
| 4,940,840 A | 7/1990 | Suslow | |
| 4,964,894 A | 10/1990 | Freepons | |
| 4,978,381 A | 12/1990 | Hadwiger | |
| 5,026,417 A | 6/1991 | Kucey | |
| 5,057,141 A | 10/1991 | Rodriquez-Kabana | |
| 5,104,437 A | 4/1992 | Hadwiger | |
| 5,141,745 A | 8/1992 | Rolfe | |
| 5,175,149 A | 12/1992 | Stacey | |
| 5,321,011 A | 6/1994 | Stacey | |

(Continued)

FOREIGN PATENT DOCUMENTS

| | | |
|---|---|---|
| CA | 2202024 A1 | 10/1998 |
| CN | 101092315 A | 12/2007 |

(Continued)

OTHER PUBLICATIONS

Halford, Chem. Eng. News, 2010, 88 (15), pp. 37-38.

(Continued)

*Primary Examiner* — Jennifer A Smith
(74) *Attorney, Agent, or Firm* — Adam L. Rucker

(57) ABSTRACT

Disclosed are methods of enhancing plant growth, comprising treating seed at least one month prior to planting with an effective amount of a plant signal molecule, wherein upon harvesting the plant exhibits at least one of increased plant yield measured in terms of bushels/acre, increased root number, increased root length, increased root mass, increased root volume and increased leaf area, compared to plants harvested from untreated seed, or compared to plants harvested from seed treated with the signal molecule just prior to or within a week or less of planting.

27 Claims, 3 Drawing Sheets

Surface area means of first-trifoliate leaves on 19-day old soybeans untreated and pretreated with Optimze

(56) References Cited

U.S. PATENT DOCUMENTS

| | | | |
|---|---|---|---|
| 5,374,627 A | 12/1994 | Ito | |
| 5,454,464 A | 10/1995 | Yamamoto | |
| 5,536,155 A | 7/1996 | Futaki | |
| 5,549,718 A | 8/1996 | Lerouge | |
| 5,554,445 A | 9/1996 | Struszczyk | |
| 5,586,411 A | 12/1996 | Gleddie | |
| 5,628,810 A | 5/1997 | Dugast | |
| 5,646,018 A | 7/1997 | Broughton | |
| 5,696,098 A | 12/1997 | Muraki | |
| 5,702,752 A | 12/1997 | Gugger | |
| 5,705,634 A | 1/1998 | Bredehorst | |
| 5,720,793 A | 2/1998 | Kato | |
| 5,726,123 A | 3/1998 | Heinsohn | |
| 5,733,851 A | 3/1998 | Villanueva | |
| 5,830,459 A | 11/1998 | Cuero | |
| 5,922,316 A | 7/1999 | Smith | |
| 5,965,545 A | 10/1999 | Ben-Shalom | |
| 5,990,291 A | 11/1999 | Waggle | |
| 6,060,429 A | 5/2000 | Ben-Shalom | |
| 6,146,668 A | 11/2000 | Kelly | |
| 6,167,652 B1 | 1/2001 | Heinsohn | |
| 6,193,988 B1 | 2/2001 | Stoner | |
| 6,197,942 B1 | 3/2001 | Muraki | |
| 6,200,929 B1 | 3/2001 | Horibe | |
| 6,242,381 B1 | 6/2001 | van der Krieken | |
| 6,258,749 B1 | 7/2001 | Nonomura | |
| 6,306,835 B1 | 10/2001 | Daly | |
| 6,352,727 B1 | 3/2002 | Takahashi | |
| 6,407,040 B1 | 6/2002 | Nichols | |
| 6,413,910 B1 | 7/2002 | Vasiljevich | |
| 6,524,998 B1 | 2/2003 | Kloepper | |
| 6,589,352 B1 | 7/2003 | Yudovsky | |
| 6,589,942 B1 | 7/2003 | Ben-Shalom | |
| 6,630,459 B2 | 10/2003 | Vournakis | |
| 6,649,566 B2 | 11/2003 | Doostdar | |
| 6,849,576 B2 | 2/2005 | Suzuki | |
| 6,878,819 B1 | 4/2005 | Natunen | |
| 6,933,380 B2 | 8/2005 | Huang | |
| 6,979,664 B1 | 12/2005 | Smith | |
| 7,098,324 B2 | 8/2006 | Haigler | |
| 7,205,450 B2 | 4/2007 | Cook | |
| 7,250,068 B1 | 7/2007 | Smith | |
| 7,262,151 B2 | 8/2007 | Smith | |
| 7,485,718 B2 | 2/2009 | Sabesan | |
| 7,521,212 B1 | 4/2009 | Samain | |
| 7,576,213 B2 | 8/2009 | Flematti | |
| 7,619,076 B2 | 11/2009 | Beau | |
| 7,637,980 B2 | 12/2009 | Smith | |
| 7,670,820 B2 | 3/2010 | Shaw | |
| 8,008,544 B2 | 8/2011 | Block | |
| 8,357,631 B2 | 1/2013 | Smith | |
| 2002/0000540 A1 | 1/2002 | Smither-Kopperl | |
| 2005/0187107 A1 | 8/2005 | Smith | |
| 2006/0277632 A1 | 12/2006 | Carr | |
| 2007/0027012 A1 | 2/2007 | Chen | |
| 2007/0105815 A1 | 5/2007 | Vournakis | |
| 2007/0238872 A1 | 10/2007 | Sabesan | |
| 2008/0057093 A1 | 3/2008 | Wan | |
| 2008/0072494 A1 | 3/2008 | Stoner | |
| 2008/0172763 A1 | 7/2008 | Jensen | |
| 2008/0248953 A1 | 10/2008 | Smith | |
| 2008/0269055 A1 | 10/2008 | Bastiaans | |
| 2009/0305895 A1* | 12/2009 | McIver et al. | 504/292 |
| 2010/0031388 A1 | 2/2010 | Tirichine | |
| 2010/0048404 A1 | 2/2010 | Hungenberg | |
| 2010/0087369 A1 | 4/2010 | Cutsem | |
| 2010/0093537 A1* | 4/2010 | Smith et al. | 504/117 |
| 2010/0099560 A1 | 4/2010 | Hnatowich | |
| 2010/0113278 A1 | 5/2010 | Suty-Heinze | |
| 2011/0301032 A1 | 12/2011 | Denarie | |
| 2012/0077674 A1* | 3/2012 | Cargeeg et al. | 504/100 |
| 2012/0322659 A1 | 12/2012 | Smith | |
| 2013/0061645 A1* | 3/2013 | Smith et al. | 71/6 |
| 2013/0109567 A1 | 5/2013 | Smith | |

FOREIGN PATENT DOCUMENTS

| | | |
|---|---|---|
| CN | 101248797 A | 8/2008 |
| CN | 101543230 A | 9/2009 |
| CN | 101601410 A | 12/2009 |
| FR | 2941591 A1 | 3/2009 |
| JP | 8003010 A2 | 1/1996 |
| WO | 89/07395 A1 | 8/1989 |
| WO | 92/17591 A1 | 10/1992 |
| WO | 98/34464 A2 | 8/1998 |
| WO | 00/04778 A1 | 2/2000 |
| WO | 01/26465 A1 | 4/2001 |
| WO | 03/077654 A1 | 9/2003 |
| WO | 2004/093542 A1 | 11/2004 |
| WO | 2005/062899 A1 | 7/2005 |
| WO | 2005/063784 A1 | 7/2005 |
| WO | WO 2005/062899 A2 | 7/2005 |
| WO | 2005/087005 A2 | 9/2005 |
| WO | 2007/006318 A2 | 1/2007 |
| WO | 2008/085958 A1 | 7/2008 |
| WO | WO 2008/085958 A1 | 7/2008 |
| WO | 2009/049747 A2 | 4/2009 |
| WO | 2010/049751 A1 | 5/2010 |
| WO | 2010/125065 A2 | 11/2010 |

OTHER PUBLICATIONS

Maj et al., 2009, J. Ecol 35:479-487.
van der Hoist et al. 2001. Current Opinions in Structural Biology 11, 608-616.
Robina et al. 2002 Tetrahedron 58, 521-530.
Samain et al. 1999, Journal of Biotechnology 72, 33-47.
Samain et al 1997, Carbohydrate Research 302, 35-42.
Cottaz et al 2005, Metabolic Engineering 7, 311-317.
Dumon et al 2006, ChemBioChem 7, 359-365.
Denaire et al 1996, Annu. Rev. Biochem. 65, 503-535.
Khan et al 2002, Photosynthetica 40(4), 621-624.
Jung et al 2007, Carbohydrate Polymers 67, 256-259.
Yoshikawa et al 1993, Plant Cell Physiol. 34(8), 1163-1173.
Hamel et al 2010, Planta 232, 787-806.
Okada et al 2002, Plant Cell Physiol 43(5), 505-512.
Muller et al 2000, Plant Physiology 124, 733-739.
Prome et al 1998, Pure & Appl. Chem. 70(1), 55-60.
Newsmart webpage re COS, www.glucosamine-chitosan.com (2005).
Darvill et al 1992, Glycobiology 2(3), 181-198.
Cote et al 1994, Plant Molecular Biology 26, 1379-1411.
Kasprezewska 2003, Cellular & Molecular Biology Letters 8, 809-824.
Cote et al 1995, Physiologiz Plantarium 93, 401-410.
Halford 2010, "Smoke Signals", Chemical & Engineering News 88(15), 1-3.
D'Haeze et al 2002, Glycobiology 12(6), 79R-105R.
Demont-Caulet et al 1999, Plant Physiology 120, 83-92.
Maillet et al 2011, Nature 469, 58-64.
Macchiavelli et al 2004, Journal of Experimental Botany 55(408), 2635-2640.
Spaink 2000, Annu. Rev. Micriobiol 54, 257-288.
Pochanavanich et al 2002, Letters in Applied Microbiology 35, 17-21.
Shaw et al 2006, Environmental Microbiology 8(11), 1867-1880.
Ralston et al 2005, Plant Physiology 137, 1375-1388.
Wakelin et al 2004, Biol Fertil Soils 40, 36-43.
Diaz et al 2000, Molecular Plant-Microbe Interactions 13(3), 268-276.
Hungria et al 1997, Soil Biol. Biochem. 29(5/6), 819-830.
Friesen et al 2005, Appl Microbiol Biotechnol 68, 397-404.
Ferguson et al 2003, J Plant Growth Regul 22, 47-72.
Collinge et al 1993, The Plant Journal 3(1), 31-40.
Leibovitch et al 2001, J Agronomy & Crop Science 187, 281-292.
Prithiviraj et al 2003, Planta 216, 437-445.
Staehelin et al 1994, Proc. Natl. Acad. Sci. USA 91, 2196-2200.
Cytryn et al, 2007, J Bacteriology, 189(19), 6751-6762.

(56) References Cited

OTHER PUBLICATIONS

Deaker et al., 2007, Soil Biology & Biochemistry 39 573-580.
LePrince et al, 2010, Plant Science 179 554-564.
Mabood et al, 2006, Field Crops Research, 95 412-419.
Mary et al, 1994, Soil Biol Biochem 26(9), 1125-1132.
Radwan et al, 2007, Intl J Phytoremediation 9, 475-486.
Streeter, 2003, J Appl Microbiol 95, 484-491.
Sugawara et al, 2010, Appl Environ Microbiol 76(4), 1071-1081.
Supanjani et al, 2006 Plant Physiology and Biochemistry, 44 866-872.
Zahran., 2001, Journal of Biotechnology, 91 143-153.
Yong et al, 2011, Fine Chem 28(5), 479-483.
Jian-ping et al, 2011, J Anhui Agric Sci 39(1), 88-89.
Noreen et al, 2003, Funct Plant Biol 30, 1219-1232.
Pedersen presentation Iowa State University "Soybean Growth and Development" (May 2009).

\* cited by examiner

SEED TREATMENT METHODS AND COMPOSITIONS

CROSS-REFERENCE TO RELATED APPLICATIONS

This application claims priority or the benefit under 35 U.S.C. 119 of U.S. provisional application Nos. 61/532,234 filed on Sep. 8, 2011 and 61/568,435 filed on Dec. 8, 2011, the contents of which are fully incorporated herein by reference.

BACKGROUND OF THE INVENTION

The symbiosis between the gram-negative soil bacteria, Rhizobiaceae and Bradyrhizobiaceae, and legumes such as soybean, is well documented. The biochemical basis for these relationships includes an exchange of molecular signaling, wherein the plant-to-bacteria signal compounds include flavones, isoflavones and flavanones, and the bacteria-to-plant signal compounds, which include the end products of the expression of the Bradyrhizobial and Rhizobial nod genes, known as lipo-chitooligosaccharides (LCOs). The symbiosis between these bacteria and the legumes enables the legume to fix atmospheric nitrogen and thereby grow in soil that has low assimilable nitrogen levels, thus obviating a need for nitrogen fertilizers. Since nitrogen fertilizers can significantly increase the cost of crops and are associated with a number of polluting effects, the agricultural industry continues its efforts to exploit this biological relationship and develop new agents and methods for improving plant yield without increasing the use of nitrogen-based fertilizers.

U.S. Pat. No. 6,979,664 teaches a method for enhancing seed germination or seedling emergence of a plant crop, comprising the steps of providing a composition that comprises an effective amount of at least one lipo-chitooligosaccharide and an agriculturally suitable carrier and applying the composition in the immediate vicinity of a seed or seedling in an effective amount for enhancing seed germination of seedling emergence in comparison to an untreated seed or seedling.

Further development on this concept is taught in WO 2005/062899, directed to combinations of at least one plant inducer, namely an LCO, in combination with a fungicide, insecticide, or combination thereof, to enhance a plant characteristic such as plant stand, growth, vigor and/or yield. The compositions and methods are taught to be applicable to both legumes and non-legumes, and may be used to treat a seed (just prior to planting), seedling, root or plant.

Similarly, WO 2008/085958 teaches compositions for enhancing plant growth and crop yield in both legumes and non-legumes, and which contain LCOs in combination with another active agent such as a chitin or chitosan, a flavonoid compound, or an herbicide, and which can be applied to seeds and/or plants concomitantly or sequentially. As in the case of the '899 Publication, the '958 Publication teaches treatment of seeds just prior to planting.

A number of other publications describe the benefit of LCOs in seed treatment processes, such as, Kidaj et al., "Nod factors stimulate seed germination and promote growth and nodulation of pea and vetch under competitive conditions," Microbiol Res 25426 (2011) and Maj et al., "Pretreatment of Clover Seeds with Nod Factors Improves Growth and Nodulation of *Trifolium pratense*," J. Chem Ecol (2009) 35:479-487.

More recently, Halford, "Smoke Signals," in Chem. Eng. News (Apr. 12, 2010), at pages 37-38, reports that karrikins or butenolides which are contained in smoke act as growth stimulants and spur seed germination after a forest fire, and can invigorate seeds such as corn, tomatoes, lettuce and onions that had been stored. These molecules are the subject of U.S. Pat. No. 7,576,213.

BRIEF SUMMARY OF THE INVENTION

The present invention provides methods of enhancing plant growth and crop production in which the beneficial effect of a plant signal molecule (plant growth-enhancing agent) may be obtained without the need to apply the plant signal molecule (plant growth-enhancing agent) to the seed contemporaneously with planting. The present invention is based, in part, on the discovery that treatment of seeds with a plant signal molecule such as an LCO, followed by prolonged storage prior to planting, results in enhanced plant growth, including greater plant yield and/or leaf surface area and/or root number, length and mass, compared to plants harvested from both untreated seeds. The present invention also provides methods of enhancing plant growth and crop production in which additional improvements may be obtained over plants crops produced from seeds treated just prior to or within a week or less of planting.

A first aspect of the present invention is directed to a method of enhancing plant growth, comprising treating seed at least one month (thirty days) prior to planting with an effective amount of a plant signal molecule. In embodiments, the seed may be treated in accordance with the present method at 2 months prior to planting, at least 3 months prior to planting, at least 4 months prior to planting, at least 5 months prior to planting, at least 6 months prior to planting, at least 9 months prior to planting, at least 1 year prior to planting, at least 2 years prior to planting and in some embodiments, at least 3 years prior to planting.

The treatment is used to produce a plant (crop) that exhibits at least one of increased yield measured in terms of bushels/acre, increased root number, increased root length, increased root mass, increased root volume and increased leaf area, compared to plants harvested from untreated seed. In particular embodiments, the treatment may be used to produce a plant (crop) that exhibits at least one of increased yield measured in terms of bushels/acre, increased root number, increased root length, increased root mass, increased root volume and increased leaf area compared to a plant (crop harvested from seed treated with the signal molecule just prior to or within a week or less of planting.

In certain embodiments of the present invention, the plant signal molecule is a lipo-chitooligosaccharide (LCO). In some embodiments, the LCO is recombinant. In other embodiments, the LCO is synthetic. In other embodiments, the LCO is obtained from a microorganism, e.g., a species of *Rhizobium* selected from *Rhizobium* sp., *Bradyrhizobium* sp., e.g., *Bradyrhizobium japonicum*, *Sinorhizobium* sp. and *Azorhizobium* sp, or from an arbuscular mycorrhizal fungus.

In other embodiments, the plant signal molecule is a chitinous compound such as a chito-oligomer (CO). In some embodiments, the CO is recombinant. In other embodiments, the CO is synthetic. In other embodiments, the CO is obtained from a microorganism as per LCO's.

In other embodiments, the plant signal molecule is a flavonoid. In other embodiments, the plant signal molecule is jasmonic acid, linoleic acid, linolenic acid or a derivative thereof. In other embodiments, the plant signal molecule is a karrikin.

Combinations of two or more different plant signal molecules (or types thereof) may be used to treat the seed.

In other embodiments, the treating further comprises contacting the seed with at least one other agronomically beneficial agent, e.g., diazotroph (Rhizobial inoculant), mycorrhizal fungi, a phosphate solubilizing agent, herbicide, insecticide or a fungicide. In some embodiments, the treating entails spraying a composition comprising the plant signal molecule onto the seed, and in some other embodiments, the treating entails dripping the composition onto the seeds.

The method of the present invention is applicable to legumes and non-legumes alike. In some embodiments, the leguminous seed is soybean seed. In some other embodiments, the seed that is treated is non-leguminous seed such as a field crop seed, e.g., corn, or a vegetable crop seed.

The seed may be treated in accordance with the present method anywhere from one month (thirty days) up to 1 year, 2 years and in some embodiments, even 3 years prior to planting, depending on particular seed properties (viability after storage) or industry standards. For example, soybean seeds are generally planted the following season, whereas corn seed can be stored for much longer periods of time including upwards of 3 years prior to planting.

The present invention also relates to seeds treated with a plant signal molecule/plant growth-enhancing agent, such as an LCO or CO, which have been stored for at least thirty-days up to 1 year, 2 years and in some embodiments, even 3 years prior to planting.

Yet another aspect of the present invention is directed to a planted seed which was treated with a plant signal molecule/plant growth-enhancing agent, such as an LCO or CO, which have been stored for at least thirty-days up to 1 year, 2 years and in some embodiments, even 3 years prior to planting.

A related aspect of the present invention is directed to a package comprising the treated seeds according to the present invention for purposes of planting subsequent to the treatment.

As demonstrated in the working examples, which include comparative experiments conducted under both greenhouse and field conditions, the benefits of signal molecules/plant growth-enhancing agents may be obtained even though the signal molecules are applied to a seed significantly prior to the time of planting and after prolonged storage period.

As further demonstrated in the working examples, which include comparative experiments conducted under both greenhouse and field conditions, embodiments of the present invention that entailed treatment of soybean seed with an LCO from *Bradyrhizobium japonicum* exhibited increased plant yield, leaf surface area, and increased root length and root volume compared to both untreated seed and seed treated with the LCO just prior to or within a week of planting.

DETAILED DESCRIPTION

Figure 1:
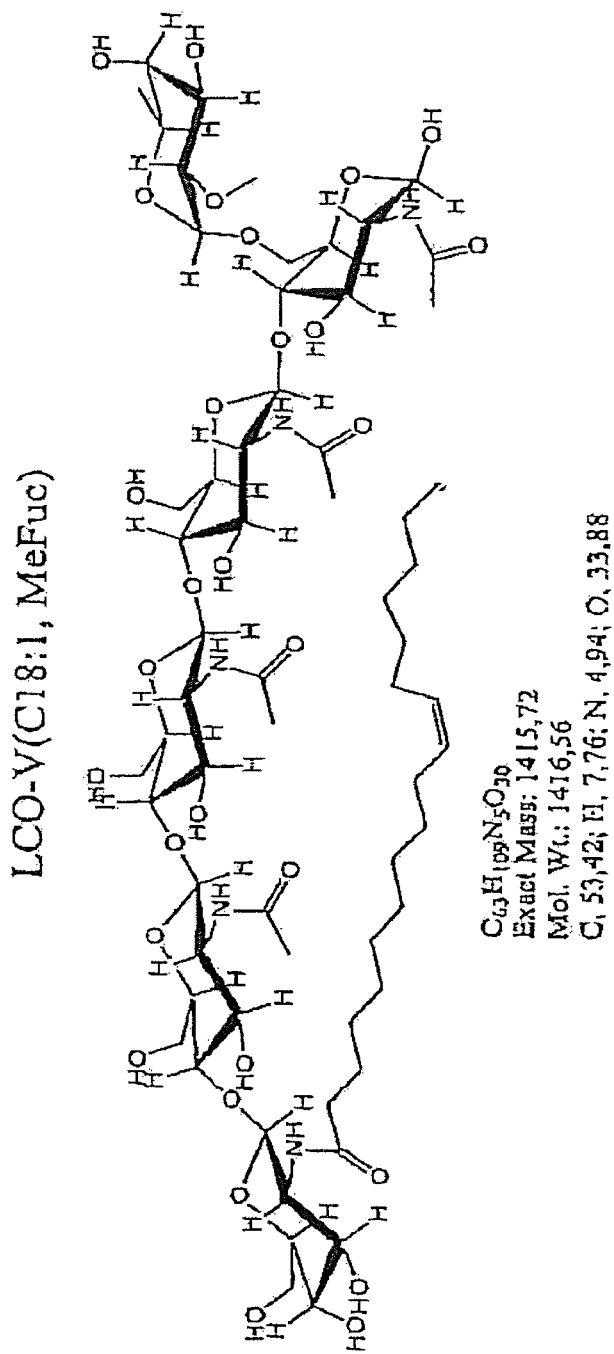
FIGS. 1 and 2 show the chemical structures of lipo-chitooligosaccharide compounds (LCO) useful in the practice of the present invention.

For purposes of the present invention, the term "plant signal molecule", which may be used interchangeably with "plant growth-enhancing agent" broadly refers to any agent, both naturally occurring in plants or microbes, and synthetic (and which may be non-naturally occurring) that directly or indirectly activates a plant biochemical pathway, resulting in increased plant growth, measurable at least in terms of at least one of increased yield measured in terms of bushels/acre, increased root number, increased root length, increased root mass, increased root volume and increased leaf area. Representative examples of plant signal molecules that may be useful in the practice of the present invention include lipo-chitooligosaccharide compounds (LCO's), chito-oligosaccharides (COs), chitinous compounds, flavonoids, jasmonic acid, linoleic acid and linolenic acid and their derivatives, and karrikins.

The plant signal molecule may be isolated and/or purified component. The term "isolated" means the signal molecule is removed from its natural state and separated from other molecules naturally associated with it. The term "purified" means that the concentration of the signal molecule is increased (by a purification process) relative to other components, e.g., unwanted or inferior components.

LCO's, also known in the art as symbiotic Nod signals or Nod factors, consist of an oligosaccharide backbone of β-1, 4-linked N-acetyl-D-glucosamine ("GlcNAc") residues with an N-linked fatty acyl chain condensed at the non-reducing end. LCO's differ in the number of GlcNAc residues in the backbone, in the length and degree of saturation of the fatty acyl chain, and in the substitutions of reducing and nonreducing sugar residues. An example of an LCO is presented below as formula I

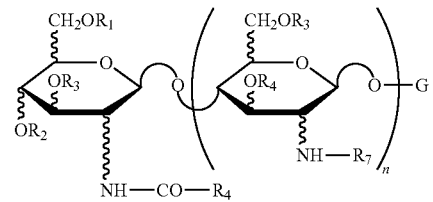

in which:

G is a hexosamine which can be substituted, for example, by an acetyl group on the nitrogen, a sulfate group, an acetyl group and/or an ether group on an oxygen, $R_1$, $R_2$, $R_3$, $R_5$, $R_6$ and $R_7$, which may be identical or different, represent H, $CH_3CO-$, $C_xH_yCO-$ where x is an integer between 0 and 17, and y is an integer between 1 and 35, or any other acyl group such as for example a carbamyl, $R_4$ represents a mono-, di-, or triunsaturated and tetraunsaturated aliphatic chain containing at least 12 carbon atoms, and n is an integer between 1 and 4.

LCOs may be obtained (e.g., isolated and/or purified) from bacteria such as *Rhizobia*, e.g., *Rhizobium* sp., *Bradyrhizobium* sp., *Sinorhizobium* sp. and *Azorhizobium* sp. LCO structure is characteristic for each such bacterial species, and each strain may produce multiple LCO's with different structures. For example, specific LCOs from *S. meliloti* have also been described in U.S. Pat. No. 5,549,718 as having the formula II:

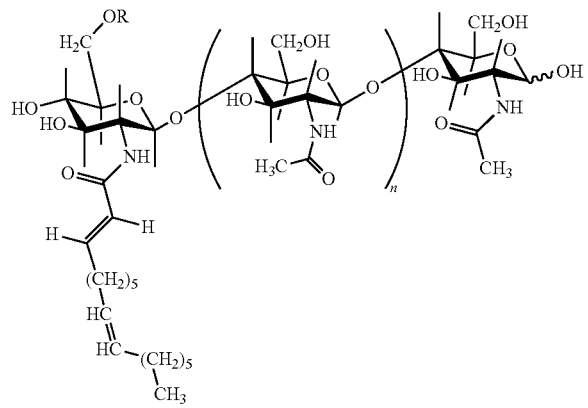

in which R represents H or CH₃CO— and n is equal to 2 or 3.

Even more specific LCOs include NodRM, NodRM-1, NodRM-3. When acetylated (the R=CH₃CO—), they become AcNodRM-1, and AcNodRM-3, respectively (U.S. Pat. No. 5,545,718).

LCOs from *Bradyrhizobium japonicum* are described in U.S. Pat. Nos. 5,175,149 and 5,321,011. Broadly, they are pentasaccharide phytohormones comprising methylfucose. A number of these *B. japonicum*-derived LCOs are described: BjNod-V ($C_{18:1}$); BjNod-V ($A_C$, $C_{18:1}$), BjNod-V ($C_{16:1}$); and BjNod-V ($A_C$, $C_{16:0}$), with "V" indicating the presence of five N-acetylglucosamines; "Ac" an acetylation; the number following the "C" indicating the number of carbons in the fatty acid side chain; and the number following the ":" the number of double bonds.

LCO's used in embodiments of the invention may be recovered from bacterial strains that produce LCO's, such as strains of *Azorhizobium, Bradyrhizobium* (including *B. japonicum*), *Mesorhizobium, Rhizobium* (including *R. leguminosarum*), *Sinorhizobium* (including *S. meliloti*), and bacterial strains genetically engineered to produce LCO's.

LCO's are the primary determinants of host specificity in legume symbiosis (Diaz, et al., Mol. Plant-Microbe Interactions 13:268-276 (2000)). Thus, within the legume family, specific genera and species of *rhizobia* develop a symbiotic nitrogen-fixing relationship with a specific legume host. These plant-host/bacteria combinations are described in Hungria, et al., Soil Biol. Biochem. 29:819-830 (1997), Examples of these bacteria/legume symbiotic partnerships include *S. meliloti*/alfalfa and sweet clover; *R. leguminosarum* biovar viciae/peas and lentils; *R. leguminosarum* biovar phaseoli/beans; *Bradyrhizobium japonicum*/soybeans; and *R. leguminosarum* biovar trifolii/red clover. Hungria also lists the effective flavonoid Nod gene inducers of the rhizobial species, and the specific LCO structures that are produced by the different rhizobial species. However, LCO specificity is only required to establish nodulation in legumes. In the practice of the present invention, use of a given LCO is not limited to treatment of seed of its symbiotic legume partner, in order to achieve increased plant yield measured in terms of bushels/acre, increased root number, increased root length, increased root mass, increased root volume and increased leaf area, compared to plants harvested from untreated seed, or compared to plants harvested from seed treated with the signal molecule just prior to or within a week or less of planting.

Thus, by way of example, an LCO obtained from *B. japonicum* may be used to treat leguminous seed other than soybean and non-leguminous seed such as corn. As another example, the pea LCO obtainable from *R. leguminosarum* illustrated in FIG. 1 (designated LCO-V (C18:1), SP104) can be used to treat leguminous seed other than pea and non-legumes too.

Also encompassed by the present invention is use of LCOs obtained (e.g., isolated and/or purified) from arbuscular mycorrhizal fungi, such as fungi of the group Glomerocycota, e.g., *Glomus intraradicus*. The structures of representative LCOs obtained from these fungi are described in WO 2010/049751 and WO 2010/049751 (the LCOs described therein also referred to as "Myc factors").

Further encompassed by the present invention is use of synthetic LCO compounds, such as those described in WO2005/063784, and recombinant LCO's produced through genetic engineering. The basic, naturally occurring LCO structure may contain modifications or substitutions found in naturally occurring LCO's, such as those described in Spaink, Crit. Rev. Plant Sci. 54:257-288 (2000) and D'Haeze, et al., Glycobiology 12:79R-105R (2002). Precursor oligosaccharide molecules (COs, which as described below, are also useful as plant signal molecules in the present invention) for the construction of LCOs may also be synthesized by genetically engineered organisms, e.g., as in Samain, et al., Carb. Res. 302:35-42 (1997).

Figure 2:
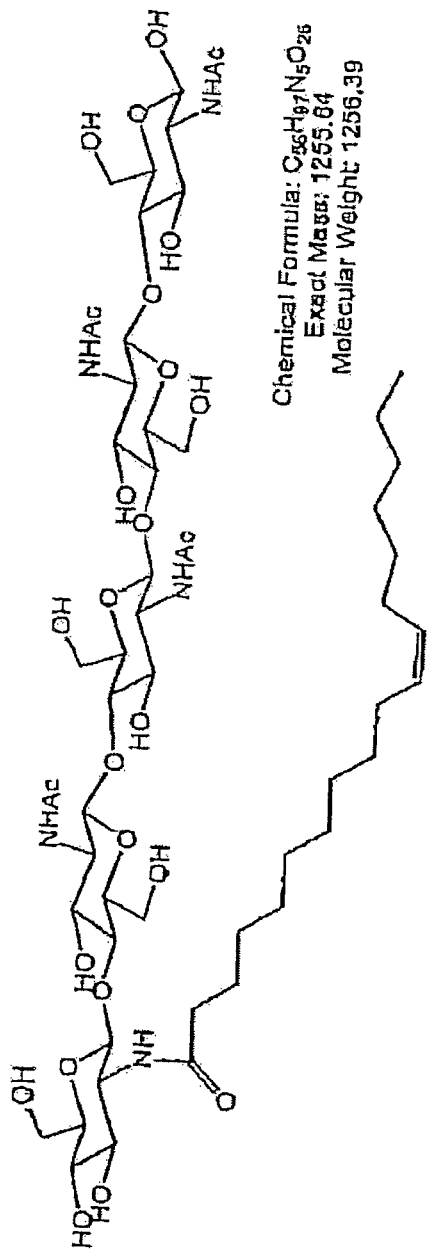

LCO's may be utilized in various forms of purity and may be used alone or in the form of a culture of LCO-producing bacteria or fungi. For example, OPTIMIZE® (commercially available from Novozymes BioAg Limited) contains a culture of *B. japonicum* that produces an LCO (LCO-V (C18:1, MeFuc), MOR116) that is illustrated in FIG. 2. Methods to provide substantially pure LCO's include simply removing the microbial cells from a mixture of LCOs and the microbe, or continuing to isolate and purify the LCO molecules through LCO solvent phase separation followed by HPLC chromatography as described, for example, in U.S. Pat. No. 5,549,718. Purification can be enhanced by repeated HPLC, and the purified LCO molecules can be freeze-dried for long-term storage.

Chitins and chitosans, which are major components of the cell walls of fungi and the exoskeletons of insects and crustaceans, are also composed of GlcNAc residues. Chitinous compounds include chitin, (IUPAC: N-[5-[[3-acetylamino-4,5-dihydroxy-6-(hydroxymethyl)oxan-2-yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), and chitosan, (IUPAC: 5-amino-6-[5-amino-6-[5-amino-4,6-dihydroxy-2(hydroxymethyl)oxan-3-yl]oxy-4-hydroxy-2-(hydroxymethyl)oxan-3-yl]oxy-2(hydroxymethyl)oxane-3,4-diol). These compounds may be obtained commercially, e.g., from Sigma-Aldrich, or prepared from insects, crustacean shells, or fungal cell walls. Methods for the preparation of chitin and chitosan are known in the art, and have been described, for example, in U.S. Pat. No. 4,536,207 (preparation from crustacean shells), Pochanavanich, et al., Lett. Appl. Microbiol. 35:17-21 (2002) (preparation from fungal cell walls), and U.S. Pat. No. 5,965, 545 (preparation from crab shells and hydrolysis of commercial chitosan). Deacetylated chitins and chitosans may be obtained that range from less than 35% to greater than 90% deacetylation, and cover a broad spectrum of molecular weights, e.g., low molecular weight chitosan oligomers of less than 15 kD and chitin oligomers of 0.5 to 2 kD; "practical grade" chitosan with a molecular weight of about 150 kD; and high molecular weight chitosan of up to 700 kD. Chitin and chitosan compositions formulated for seed treatment are also commercially available. Commercial products include, for example, ELEXA® (Plant Defense Boosters, Inc.) and BEYOND™ (Agrihouse, Inc.).

Yet other chitinous compounds that are suitable for use in the present invention include COs (e.g., isolated and/or purified). COs are known in the art as R-1-4 linked N actyl glucosamine structures identified as chitin oligomers, also as N-acetylchitooligosaccharides. CO's have unique and different side chain decorations which make them different from chitin molecules [$(C_8H_{13}NO_5)$n, CAS No. 1398-61-4], and chitosan molecules [$(C_5H_{11}NO_4)$n, CAS No. 9012-76-4]. Representation literature describing the structure and production of COs is as follows: Van der Holst, et al., Current Opinion in Structural Biology, 11:608-616 (2001); Robina, et al., Tetrahedron 58:521-530 (2002); Hanel, et al., Planta 232: 787-806 (2010); Rouge, et al. Chapter 27, "The Molecular Immunology of Complex Carbohydrates" in Advances in Experimental Medicine and Biology, Springer Science; Wan, et al., Plant Cell 21:1053-69 (2009); PCT/F100/00803 (Sep. 21, 2000); and Demont-Caulet, et al., Plant Physiol. 120(1): 83-92 (1999). Two COs suitable for use in the present invention may be easily derived from the LCOs shown in FIGS. 1 and 2 (minus the fatty acid chains), which are the CO precursors to the LCOs shown in FIGS. 1 and 2. Methods for preparation of recombinant COs are known in the art. See, e.g., Samain, et al. (supra.); Cottaz, et al., Meth. Eng. 7(4): 311-7 (2005) and Samain, et al., J. Biotechnol. 72:33-47 (1999).

Flavonoids are phenolic compounds having the general structure of two aromatic rings connected by a three-carbon bridge. Flavonoids are produced by plants and have many functions, e.g., as beneficial signaling molecules, and as protection against insects, animals, fungi and bacteria. Classes of flavonoids include chalcones, anthocyanidins, coumarins, flavones, flavanols, flavonols, flavanones, and isoflavones. See, Jain, et al., J. Plant Biochem. & Biotechnol. 11:1-10 (2002); Shaw, et al., Environmental Microbiol. 11:1867-80 (2006).

Representative flavonoids that may be useful in the practice of the present invention include genistein, daidzein, formononetin, naringenin, hesperetin, luteolin, and apigenin. Flavonoid compounds are commercially available, e.g., from Natland International Corp., Research Triangle Park, N.C.; MP Biomedicals, Irvine, Calif.; LC Laboratories, Woburn Mass. Flavonoid compounds may be isolated from plants or seeds, e.g., as described in U.S. Pat. Nos. 5,702,752; 5,990, 291; and 6,146,668. Flavonoid compounds may also be produced by genetically engineered organisms, such as yeast, as described in Ralston, et al., Plant Physiology 137:1375-88 (2005).

In other embodiments, the seed are treated with jasmonic acid (JA, [1R-[1α,2β(Z)]]-3-oxo-2-(pentenyl)cyclopentaneacetic acid) and its derivatives, linoleic acid ((Z,Z)-9,12-Octadecadienoic acid) and its derivatives, and linolenic acid ((Z,Z,Z)-9,12,15-octadecatrienoic acid) and its derivatives. Jasmonic acid and its methyl ester, methyl jasmonate (MeJA), collectively known as jasmonates, are octadecanoid-based compounds that occur naturally in plants. Jasmonic acid is produced by the roots of wheat seedlings, and by fungal microorganisms such as *Botryodiplodia theobromae* and *Gibbrella fujikuroi*, yeast (*Saccharomyces cerevisiae*), and pathogenic and non-pathogenic strains of *Escherichia coli*. Linoleic acid and linolenic acid are produced in the course of the biosynthesis of jasmonic acid. Jasmonates, linoleic acid and linoleic acid (and their derivatives) are reported to be inducers of nod gene expression or LCO production by rhizobacteria. See, e.g., Mabood, Fazli, Jasmonates induce the expression of nod genes in *Bradyrhizobium japonicum*, May 17, 2001; and Mabood, Fazli, "Linoleic and linolenic acid induce the expression of nod genes in *Bradyrhizobium japonicum*," USDA 3, May 17, 2001.

Useful derivatives of linoleic acid, linolenic acid, and jasmonic acid that may be useful in the practice of the present invention include esters, amides, glycosides and salts. Representative esters are compounds in which the carboxyl group of linoleic acid, linolenic acid, or jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a—COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid, and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salt may be precipitated from solution and be collected by filtration or may be recovered by other means such as by evaporation of the solvent.

In other embodiments, the seed are treated with a vinylogous 4H-pyrone e.g., 2H-furo[2,3-c]pyran-2-ones including derivatives and analogues thereof, examples of which are represented by the following structure:

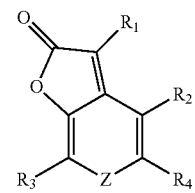

wherein; Z is O, S or NR$_5$; R$_1$, R$_2$, R$_3$, and R$_4$ are each independently H, alkyl, alkenyl, alkynyl, phenyl, benzyl, hydroxy, hydroxyalkyl, alkoxy, phenyloxy, benzyloxy, CN, COR$_6$, COOR=, halogen, NR$_6$R$_7$, or NO$_2$; and R$_5$, R$_6$, and $R_7$ are each independently H, alkyl or alkenyl, or a biologically acceptable salt thereof. Examples of biologically acceptable salts of these compounds may include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by the structure and which may be suitable for use in the present invention include the following: 3-methyl-2H-furo[2,3-c]pyran-2-one (where $R_1=CH_3$, $R_2$, $R_3$, $R_4=H$), 2H-furo[2,3-c]pyran-2-one (where $R_1$, $R_2$, $R_3$, $R_4=H$), 7-methyl-2H-furo[2,3-c]pyran-2-one (where $R_1$, $R_2$, $R_4=H$, $R_3=CH_3$), 5-methyl-2H-furo[2,3-c]pyran-2-one (where $R_1$, $R_2$, $R_3=H$, $R_4=CH_3$), 3,7-dimethyl-2H-furo[2,3-c]pyran-2-one (where $R_1$, $R_3=CH_3$, $R_2$, $R_4=H$), 3,5-dimethyl-2H-furo[2,3-c]pyran-2-one (where $R_1$, $R_4=CH_3$, $R_2$, $R_3=H$), 3,5,7-trimethyl-2H-furo[2,3-c]pyran-2-one (where $R_1$, $R_3$, $R_4=CH_3$, $R_2=H$), 5-methoxymethyl-3-methyl-2H-furo[2,3-c]pyran-2-one (where $R_1=CH_3$, $R_2$, $R_3=H$, $R_4=CH_2OCH_3$), 4-bromo-3,7-dimethyl-2H-furo[2,3-c]pyran-2-one (where $R_1$, $R_3=CH_3$, $R_2=Br$, $R_4=H$), 3-methylfuro[2,3-c]pyridin-2(3H)-one (where Z=NH, $R_1=CH_3$, $R_2$, $R_3$, $R_4=H$), 3,6-dimethylfuro[2,3-c]pyridin-2(6H)-one (where Z=N—$CH_3$, $R_1=CH_3$, $R_2$, $R_3$, $R_4=H$). See, U.S. Pat. No. 7,576,213. These molecules are also known as karrikins. See, Halford, supra.

Seeds may be treated with the plant signal molecule in several ways but preferably via spraying or dripping. Spray and drip treatment may be conducted by formulating an effective amount of the plant signal molecule in an agriculturally acceptable carrier, typically aqueous in nature, and spraying or dripping the composition onto seed via a continuous treating system (which is calibrated to apply treatment at a predefined rate in proportion to the continuous flow of seed), such as a drum-type of treater. These methods advantageously employ relatively small volumes of carrier so as to allow for relatively fast drying of the treated seed. In this fashion, large volumes of seed can be efficiently treated. Batch systems, in which a predetermined batch size of seed and signal molecule compositions are delivered into a mixer, may also be employed. Systems and apparati for performing these processes are commercially available from numerous suppliers, e.g., Bayer CropScience (Gustafson).

In another embodiment, the treatment entails coating seeds. One such process involves coating the inside wall of a round container with the composition, adding seeds, then rotating the container to cause the seeds to contact the wall and the composition, a process known in the art as "container coating". Seeds can be coated by combinations of coating methods. Soaking typically entails use of an aqueous solution containing the plant growth enhancing agent. For example, seeds can be soaked for about 1 minute to about 24 hours (e.g., for at least 1 min, 5 min, 10 min, 20 min, 40 min, 80 min, 3 hr, 6 hr, 12 hr, 24 hr). Some types of seeds (e.g., soybean seeds) tend to be sensitive to moisture. Thus, soaking such seeds for an extended period of time may not be desirable, in which case the soaking is typically carried out for about 1 minute to about 20 minutes.

Without intending to be bound by any particular theory of operation, Applicants believe that even to the extent that the treating may not cause the plant signal molecule to remain in contact with the seed surface after treatment and during any part of storage, the signal molecule may achieve intended effects by a phenomenon known as seed memory or seed perception. See, Macchiavelli and Brelles-Marino, J. Exp. Bot. 55(408):2635-40 (2004). Applicants also believe that following treatment the signal molecule, e.g., the LCO, diffuses toward the young developing radical and activates symbiotic and developmental genes which results in a change in the root architecture of the plant. Notwithstanding, the compositions containing the plant signal molecule may further contain a sticking or coating agent to assist in adherence of the signal molecule to the seed. For aesthetic purposes, the compositions may further contain a coating polymer and/or a colorant.

The effective amount of the plant signal molecule used to treat the seed, expressed in units of concentration, generally ranges from about $10^{-5}$ to about $10^{-14}$ M, and in some embodiments, from about $10^{-5}$ to about $10^{-11}$ M, and in some other embodiments from about $10^{-7}$ to about $10^{-8}$ M. Expressed in units of weight, the effective amount generally ranges from about 1 to about 400 µg/hundred weight (cwt) seed, and in some embodiments from about 2 to about 70 µg/cwt, and in some other embodiments, from about 2.5 to about 3.0 µg/cwt seed. The effective amount of the plant signal molecule, however, may be obtained by a suitable dosage response assay, preferably, in a greenhouse and/or field study.

The treatment may also involve contacting the seed, prior, simultaneously with or sequentially to the contacting with the plant signal molecule, with an agriculturally/agronomically beneficial agent. As used herein and in the art, the term "agriculturally or argonomically beneficial" refers to agents that when applied to seeds result in enhancement (which may be statistically significant) of plant characteristics such as plant stand, growth, vigor or yield in comparison to non-treated seeds. Representative examples of such agents that may be useful in the practice of the present invention includes, but is not limited to, diazotrophs, mycorrhizal fungi, herbicides, fungicides, insecticides, and phosphate solubilizing agents.

Suitable herbicides include bentazon, acifluorfen, chlorimuron, lactofen, clomazone, fluazifop, glufosinate, glyphosate, sethoxydim, imazethapyr, imazamox, fomesafe, flumiclorac, imazaquin, and clethodim. Commercial products containing each of these compounds are readily available. Herbicide concentration in the composition will generally correspond to the labeled use rate for a particular herbicide.

A "fungicide" as used herein and in the art, is an agent that kills or inhibits fungal growth. As used herein, a fungicide "exhibits activity against" a particular species of fungi if treatment with the fungicide results in killing or growth inhibition of a fungal population (e.g., in the soil) relative to an untreated population. Effective fungicides in accordance with the invention will suitably exhibit activity against a broad range of pathogens, including but not limited to *Phytophthora, Rhizoctonia, Fusarium, Pythium, Phomopsis* or *Selerotinia* and *Phakopsora* and combinations thereof.

Commercial fungicides may be suitable for use in the present invention. Suitable commercially available fungicides include PROTÉGÉ, RIVAL or ALLEGIANCE FL or LS (Gustafson, Plano, Tex.), WARDEN RTA (Agrilance, St. Paul, Minn.), APRON XL, APRON MAXX RTA or RFC, MAXIM 4FS or XL (Syngenta, Wilmington, Del.), CAPTAN (Arvesta, Guelph, Ontario) and PROTREAT (Nitragin Argentina, Buenos Ares, Argentina). Active ingredients in these and other commercial fungicides include, but are not limited to, fludioxonil, mefenoxam, azoxystrobin and metalaxyl. Commercial fungicides are most suitably used in accordance with the manufacturer's instructions at the recommended concentrations.

As used herein, an insecticide "exhibits activity against" a particular species of insect if treatment with the insecticide results in killing or inhibition of an insect population relative to an untreated population. Effective insecticides in accordance with the invention will suitably exhibit activity against a broad range of insects including, but not limited to, wireworms, cutworms, grubs, corn rootworm, seed corn maggots, flea beetles, chinch bugs, aphids, leaf beetles, and stink bugs.

Commercial insecticides may be suitable for use in the present invention. Suitable commercially-available insecticides include CRUISER (Syngenta, Wilmington, Del.), GAUCHO and PONCHO (Gustafson, Plano, Tex.). Active ingredients in these and other commercial insecticides include thiamethoxam, clothianidin, and imidacloprid. Commercial insecticides are most suitably used in accordance with the manufacturer's instructions at the recommended concentrations.

As used herein, phosphate solubilizing agents include, but are not limited to, phosphate solubilizing microorganisms. As used herein, "phosphate solubilizing microorganism" is a microorganism that is able to increase the amount of phosphorous available for a plant. Phosphate solubilizing microorganisms include fungal and bacterial strains. In embodiment, the phosphate solubilizing microorganism is a spore forming microorganism.

Non-limiting examples of phosphate solubilizing microorganisms include species from a genus selected from the group consisting of *Acinetobacter, Arthrobacter, Arthrobotrys, Aspergillus, Azospirillum, Bacillus, Burkholderia, Candida Chryseomonas, Enterobacter, Eupenicillium, Exiguobacterium, Klebsiella, Kluyvera, Microbacteriumr, Mucor, Paecilomyces, Paenibacillus, Penicillium, Pseudomonas, Serratia, Stenotrophomonas, Streptomyces, Streptosporangiurm, Swaminathania, Thiobacillus, Torulospora, Vibrio, Xanthobacter,* and *Xanthomonas.*

Non-limiting examples of phosphate solubilizing microorganisms are selected from the group consisting *Acinetobacter calcoaceticus, Acinetobacter* sp, *Arthrobacter* sp., *Arthrobotrys oligospora, Aspergillus niger, Aspergillus* sp., *Azospirillum halopraeferans, Bacillus amyloliquefaciens, Bacillus atrophaeus, Bacillus circulans, Bacillus licheniformis, Bacillus subtilis, Burkholderia cepacia, Burkholderia vietnamiensis, Candida krissii, Chryseomonas luteola, Enterobacter aerogenes, Enterobacter asburiae, Enterobacter* sp., *Enterobacter taylorae, Eupenicillium parvum, Exiguobacterium* sp., *Klebsiella* sp., *Kluyvera cryocrescens, Microbacterium* sp., *Mucor ramosissimus, Paecilomyces hepialid, Paecilomyces marquandii, Paenibacillus macerans, Paenibacillus mucilaginosus, Pantoea aglomerans, Penicillium expansum, Pseudomonas corrugate, Pseudomonas fluorescens, Pseudomonas lutea, Pseudomonas poae, Pseudomonas putida, Pseudomonas stutzeri, Pseudomonas trivialis, Serratia marcescens, Stenotrophomonas maltophilia, Streptomyces* sp., *Streptosporangium* sp., *Swaminathania salitolerans, Thiobacillus ferrooxidans, Torulospora globosa, Vibrio proteolyticus, Xanthobacter agilis,* and *Xanthomonas campestris.*

Preferably, the phosphate solubilizing microorganism is a strain of the fungus *Penicillium.* Strains of the fungus *Penicillium* that may be useful in the practice of the present invention include *P. bilaiae* (formerly known as *P. bilaii*), *P. albidum, P. aurantiogriseum, P. chrysogenum, P. citreonigrum, P. citrinum, P. digitatum, P. frequentas, P. fuscum, P. gaestrivorus, P. glabrum, P. griseofulvum, P. implicatum, P. janthinellum, P. lilacinum, P. minioluteum, P. montanense, P. nigricans, P. oxalicum, P. pinetorum, P. pinophilum, P. purpurogenum, P. radicans, P. radicum, P. raistrickii, P. rugulosum, P. simplicissimum, P. solitum, P. variabile, P. velutinum, P. viridicatum, P. glaucum, P. fussiporus,* and *P. expansum.*

More preferably, the phosphate solubilizing microorganism *Penicillium* species is *P. bilaiae, P. gaestrivorus,* and/or a combination thereof. Most preferably, the *P. bilaiae* strains are selected from the group consisting of ATCC 20851, NRRL 50169, ATCC 22348, ATCC 18309, NRRL 50162 (Wakelin, et al., 2004. Biol Fertil Soils 40:36-43) and the *P. gaestrivorus* strain is NRRL 50170 (see, Wakelin, supra.).

According to the invention, it is envisioned that more than one phosphate solubilizing microorganism may be used, such as, at least two, at least three, at least four, at least five, at least six, including any combination of the *Acinetobacter, Arthrobacter, Arthrobotrys, Aspergillus, Azospirillum, Bacillus, Burkholderia, Candida Chryseomonas, Enterobacter, Eupenicillium, Exiguobacterium, Klebsiella, Kluyvera, Microbacterium, Mucor, Paecilomyces, Paenibacillus, Penicillium, Pseudomonas, Serratia, Stenotrophomonas, Streptomyces, Streptosporangium, Swaminathania, Thiobacillus, Torulospora, Vibrio, Xanthobacter,* and *Xanthomonas,* including one species selected from the following group: *Acinetobacter calcoaceticus, Acinetobacter* sp, *Arthrobacter* sp., *Arthrobotrys oligospora, Aspergillus niger, Aspergillus* sp., *Azospirillum halopraeferans, Bacillus amyloliquefaciens, Bacillus atrophaeus, Bacillus circulans, Bacillus licheniformis, Bacillus subtilis, Burkholderia cepacia, Burkholderia vietnamiensis, Candida krissii, Chryseomonas luteola, Enterobacter aerogenes, Enterobacter asburiae, Enterobacter* sp., *Enterobacter taylorae, Eupenicillium parvum, Exiguobacterium* sp., *Klebsiella* sp., *Kluyvera cryocrescens, Microbacterium* sp., *Mucor ramosissimus, Paecilomyces hepialid, Paecilomyces marquandii, Paenibacillus macerans, Paenibacillus mucilaginosus, Pantoea aglomerans, Penicillium expansum, Pseudomonas corrugate, Pseudomonas fluorescens, Pseudomonas lutea, Pseudomonas poae, Pseudomonas putida, Pseudomonas stutzeri, Pseudomonas trivialis, Serratia marcescens, Stenotrophomonas maltophilia, Streptomyces* sp., *Streptosporangium* sp., *Swaminathania salitolerans, Thiobacillus ferrooxidans, Torulospora globosa, Vibrio proteolyticus, Xanthobacter agilis,* and *Xanthomonas campestris.*

Diazotrophs are bacteria and archaea that fix atmospheric nitrogen gas into a more usable form such as ammonia. Examples of diazotrophs include bacteria from the genera *Rhizobium* spp. (e.g., *R. cellulosilyticum, R. daejeonense, R. etli, R. galegae, R. gallicum, R. giardinii, R. hainanense, R. huautlense, R. indigoferae, R. leguminosarum, R. loessense, R. lupini, R. lusitanum, R. meliloti, R. mongolense, R. miluonense, R. sullae, R. tropici, R. undicola,* and/or *R. yanglingense*), *Bradyrhizobium* spp. (e.g., *B. bete, B. canariense, B. elkanii, B. iriomotense, B. japonicum, B. jicamae, B. liaoningense, B. pachyrhizi,* and/or *B. yuanmingense*), *Azorhizobium* spp. (e.g., *A. caulinodans* and/or *A. doebereinerae*), *Sinorhizobium* spp. (e.g., *S. abri, S. adhaerens, S. americanum, S. aboris, S. fredii, S. indiaense, S. kostiense, S. kummerowiae, S. medicae, S. meliloti, S. mexicanus, S. morelense, S. saheli, S. terangae,* and/or *S. xinjiangense*), *Mesorhizobium* spp., (*M. albiziae, M. amorphae, M. chacoense, M. ciceri, M. huakuii, M. loti, M. mediterraneum, M. pluifarium, M. septentrionale, M. temperatum,* and/or *M. tianshanense*), and combinations thereof. In a particular embodiment, the diazotroph is selected from the group consisting of *B. japonicum, R leguminosarum, R meliloti, S. meliloti,* and combinations thereof. In another embodiment, the diazotroph is *B. japonicum.* In another embodiment, the diazotroph is *R. leguminosarum.* In another embodiment, the diazotroph is *R. meliloti.* In another embodiment, the diazotroph is *S. meliloti.*

Mycorrhizal fungi form symbiotic associations with the roots of a vascular plant, and provide, e.g., absorptive capacity for water and mineral nutrients due to the comparatively large surface area of mycelium. Mycorrhizal fungi include endomycorrhizal fungi (also called vesicular arbuscular mycorrhizae, VAMs, arbuscular mycorrhizae, or AMs), an ectomycorrhizal fungi, or a combination thereof. In one embodiment, the mycorrhizal fungi is an endomycorrhizae of the phylum Glomeromycota and genera *Glomus* and *Gigaspora*. In still a further embodiment, the endomycorrhizae is a strain of *Glomus aggregatum, Glomus brasilianum, Glomus clarum, Glomus deserticola, Glomus etunicatum, Glomus fasciculatum, Glomus intraradices, Glomus monosporum,* or *Glomus mosseae, Gigaspora margarita,* or a combination thereof.

Examples of mycorrhizal fungi include ectomycorrhizae of the phylum Basidiomycota, Ascomycota, and Zygomycota. Other examples include a strain of *Laccaria bicolor, Laccaria laccata, Pisolithus tinctorius, Rhizopogon amylopogon, Rhizopogon fulvigleba, Rhizopogon luteolus, Rhizopogon villosuli, Scleroderma cepa, Scleroderma citrinum,* or a combination thereof.

The mycorrhizal fungi include ecroid mycorrhizae, arbutoid mycorrhizae, or monotropoid mycorrhizae. Arbuscular and ectomycorrhizae form ericoid mycorrhiza with many plants belonging to the order Ericales, while some Ericales form arbutoid and monotropoid mycorrhizae. In one embodiment, the mycorrhiza may be an ericoid mycorrhiza, preferably of the phylum Ascomycota, such as *Hymenoscyphous ericae* or *Oidiodendron* sp. In another embodiment, the mycorrhiza also may be an arbutoid mycorrhiza, preferably of the phylum Basidiomycota. In yet another embodiment, the mycorrhiza may be a monotripoid mycorrhiza, preferably of the phylum Basidiomycota. In still yet another embodiment, the mycorrhiza may be an orchid mycorrhiza, preferably of the genus *Rhizoctonia*.

The methods of the present invention are applicable to leguminous seed, representative examples of which include soybean, alfalfa, peanut, pea, lentil, bean and clover. The methods of the present invention are also applicable to non-leguminous seed, e.g., Poaceae, Cucurbitaceae, Malvaceae. Asteraceae, Chenopodiaceae and Solonaceae. Representative examples of non-leguminous seed include field crops such as corn, cereals such as rice, barley and wheat, cotton and canola, and vegetable crops such as potatoes, tomatoes, cucumbers, beets, lettuce and cantaloupe.

Following treatment, and for purpose of storage, the seed is then packaged, e.g., in 50-lb or 100-lb bags, or bulk bags or containers, in accordance with standard techniques. The seed is stored for at least 1, 2, 3, 4, 5, 6, 7, 8, 9, 10, 11, or 12 months, and even longer, e.g., 13, 14, 15, 16, 17, 18, 19, 20, 21, 22, 23, 24, 25, 26, 27, 28, 29, 30, 31, 32, 33, 34, 35, 36 months, or even longer, under appropriate storage conditions which are known in the art. As used herein, the term "month" shall mean 30 days. As used herein, a year shall mean 365 days. Whereas soybean seed may have to be planted the following season, corn seed can be stored for much longer periods of time including upwards of 3 years.

The plant signal molecule may be applied in any suitable manner, such as, in the form of a seed treatment composition which comprises at least one plant signal molecule and an agriculturally acceptable carrier.

Any suitable agriculturally acceptable carrier may be used, for example, a solid carrier, semi-solid carrier, an aqueous-based liquid carrier, a non-aqueous based liquid carrier, a suspension, an emulsion or an emulsifiable concentrate. Agriculturally-acceptable carriers may include, e.g., adjuvants, inert components, dispersants, surfactants, tackifiers, binders, stabilizing agents, and/or polymers.

The seed treatment composition may further include one or more agriculturally/agronomically beneficial agents (that is in addition to the signal molecule), such as, one or more diazotrophs, mycorrhizal fungi, herbicides, fungicides, insecticides, and/or phosphate solubilizing agents.

The present invention will now be described by way of the following non-limiting examples. They are presented solely for purposes of illustration, and are not intended to limit the invention in any way.

Summary of Working Examples

Examples 1 and 2 describe comparative field experiments using soybean seed that demonstrate that the claimed invention achieves increased plant yield. Seed were treated in accordance with the present invention at 5 months prior to planting with the commercial product Optimize® which is a combination of *Bradyrhizobium japonicum* inoculant and LCO-V (C18:1, MeFuc) (illustrated in FIG. 2), and with the pure LCO alone, and at 4.5 months prior to planting with non-commercial (i.e., less pure) grades of Optimize® and the LCO alone, and for purposes of comparison with these same plant signal molecules at the time of planting. Untreated seed was used as another control. The results, which are expressed in terms of the difference in grain yield, measured in units of bushels/acre, show that the methods of the claimed invention achieved an increase in soybean yield, relative to non-inventive methods (i.e., seed treated at time of planting and non-treated seed).

Examples 3 and 4 describe comparative experiments conducted in the greenhouse and which demonstrate that the claimed invention achieves increases in other plant growth characteristics. Example 3 describes an experiment that entailed treatment of soybean seed with pure LCO-V (C18:1, MeFuc) one month and one year before planting. The soybean plants (including roots) were harvested ten days after planting. Results, which are described in terms of differences in root length and volume, show the methods of the present invention achieve dramatic increases in these properties. Lastly, Example 4 describes experiments conducted with soybean seed treated with Optimize® 55 days prior to planting and for purposes of comparison, soybean seed treated 7 days prior to planting and untreated seed. The results, expressed in units of mean surface area of first trifoliate leaves, show that the claimed invention enhances plant growth in this respect too.

Example 1

A field trial was conducted to evaluate embodiments of the present invention on grain yield when applied on soybean seed. The field trial site was located near Whitewater, Wis. and characterized by Milford silty clay loam soil. Soil testing, conducted six months prior to planting, showed a soil pH of 6.8, an organic matter content of 5.3%, and phosphorus and potassium contents of 39 ppm and 139 ppm, respectively.

The plant signal molecules used in the trial were Optimize®, a non-commercial grade of Optimize® (NI-50S-1), pure LCO-V (C18:1, MeFuc) (NI-50GREN-1) and a non-commercial grade of LCO-V (C18:1, MeFuc) (NI-50S-2CF). The soybean seed used in the study was Stine S2118. The plant signal molecules were sprayed onto seeds with/without dilution at a rate of 4.8 fl oz/cwt.

The study was conducted in a randomized complete block design, with a plot size of 10 feet by 50 feet (0.011 acres), with 7.5-inch row spacing. Four replications were conducted. Seed were treated with the plant signal molecules 4.5 or 5 months prior to planting and just prior to planting, and were planted at a depth of 1 inch and at a seedling rate of 225,000 seeds per acre using a John Deere 750 NT grain drill. The pesticides Extreme® and AMPS® were both applied 11 days prior to planting (pre-emergence) at rates of 3.0 pt and 2.5 lb, respectively. Assure II, Roundup WeatherMax® and AMPS® were all applied 46-days post-planting (post-emergent), at rates of 6.0 oz, 21 oz and 2.5 lb, respectively. Plants were harvested 4 months and 20 days after planting.

The Control seed was treated with an amount (wt) of water, corresponding to the amount (wt) of the experimental signal molecule composition (signal molecule+carrier). The Control seed was stored under the same conditions as the experimental seed prior to planting and planted at the same time as the experimental seed in the same soil.

Results of the study are shown in Table 1 below.

TABLE 1

|   | TREATMENT GROUP | GRAIN YIELD @ 13% |
|---|---|---|
| 1 | Control - non-inoculated | 62.5 |
| 2 | Optimize - at planting | 64.2 |
| 3 | Optimize - 5 month | 65.7 |
| 4 | NI-50GREN-1 - At planting | 62.2 |
| 5 | NI-50GREN-1 - 5 month | 70.5 |
| 6 | NI-50S-1 - 4.5 month | 67.2 |
| 7 | NI-50S-2CF - 4.5 month | 69.6 |

As reflected by the comparison between comparative (non-inventive) Group 2 and inventive Group 3, treatment of the soybean seed with the commercial-grade Optimize® at 5 months pre-planting resulted in an increase in soybean yield of 1.5 bushels of soybean. As reflected by the comparison between Group 4 and inventive Group 5, treatment of soybean seed at 5 months pre-planting with pure LCO-V (C18:1, MeFuc) alone resulted in an increase in soybean yield of 8.3 bushels/acre. As reflected by the comparison between Group 2 and inventive Group 6, treatment of the soybean seeds 4.5 months prior to planting with the non-commercial grade of Optimize® resulted in an increase in soybean yield of 3.0 bushels/acre. Lastly, as shown by the comparison between Group 4 and inventive Group 7, treatment of soybean seeds with the non-commercial grade of LCO-V (C18:1, MeFuc) alone 4.5 months pre-planting increased soybean yield by 7.4 bushels/acre. Grain yield measurements were taken at a 13% seed moisture level.

Example 2

A soybean trial was conducted to evaluate embodiments of the present invention on grain yield when applied on soybean seed. The field trial site was located near Whitewater, Wis. and characterized by Milford silty clay loam soil. Soil testing, conducted six months prior to planting, showed a soil pH of 6.6, an organic matter content of 4.8%, and phosphorus and potassium contents of 41 ppm and 131 ppm, respectively.

The plant signal molecules used in the trial were same as in Example 1. The soybean seed used in the study was Stine S2118. The plant signal molecules were sprayed onto seeds with/without dilution at a rate of 4.8 fl oz/cwt.

The study was conducted in a randomized complete block design, with a plot size of 10 feet by 50 feet (0.011 acres), with 7.5-inch row spacing. Four replications were conducted. Seed were treated with the plant signal molecules 4.5 or 5 months prior to planting and just prior to planting, and were planted at a depth of 1 inch and at a seedling rate of 225,000 seeds per acre using a John Deere 750 NT grain drill. The pesticides Extreme® and AMPS® were both applied 10 days prior to planting (pre-emergence) at rates of 3.0 pt and 2.5 lb, respectively. Assure II, Roundup WeatherMax® and AMPS® were all applied 45-days post-planting (post-emergent), at rates of 6.0 oz, 21 oz and 2.5 lb, respectively. Plants were harvested 4 months and 21 days after planting.

The Control seed was treated with an amount (wt) of water, corresponding to the amount (wt) of the experimental signal molecule composition (signal molecule+carrier). The Control seed was stored under the same conditions as the experimental seed prior to planting and planted at the same time as the experimental seed in the same soil.

Results of the study are shown in Table 2 below.

TABLE 2

|   | TREATMENT GROUP | GRAIN YIELD @ 13% |
|---|---|---|
| 1 | Control - non-inoculated | 62.4 |
| 2 | Optimize - at planting | 64.1 |
| 3 | Optimize - 5 month | 68.6 |
| 4 | NI-50GREN-1 - At planting | 65.8 |
| 5 | NI-50GREN-1 - 5 month | 64.0 |
| 6 | NI-50S-1 - 4.5 month | 69.4 |
| 7 | NI-50S-2CF - 4.5 month | 66.6 |

As reflected by the comparison between comparative (non-inventive) Group 2 and inventive Group 3, treatment of the soybean seed with the commercial-grade Optimize® at 5 months pre-planting resulted in an increase in soybean yield of 4.5 bushels of soybean. As reflected by the comparison between Group 2 and inventive Group 6, treatment of the soybean seeds 4.5 months prior to planting with the non-commercial grade of Optimize® resulted in an increase in soybean yield of 5.3 bushels/acre. As shown by the comparison between Group 4 and inventive Group 7, treatment of soybean seeds with the non-commercial grade of LCO-V (C18:1, MeFuc) alone 4.5 months pre-planting increased soybean yield by 0.8 bushels/acre. The only negative response as reflected by the comparison between non-inventive Group 4 and inventive Group 5, showed that treatment of soybean seed at 5 months pre-planting with the pure LCO alone resulted in a decrease in 1.8 bushels/acre, a result attributable to unexplained variability associated with field trials. Grain yield measurements were taken at a 13% seed moisture level.

Greenhouse Experiments

Example 3

Soybean seeds treated with $10^{-7}$M pure LCO-V (C18:1, MeFuc) and stored at 15° C. Treated seeds and non-treated seeds (control) were planted 1 and 12 months after treatment in greenhouse pots containing sand:perlite (1:1 mixture). Seedlings were grown for 10 days after seed plantings then seedlings were harvested, their roots cleaned and measured on the Winrhizo® scanner. The Control seed was treated with an amount (wt) of water, corresponding to the amount (wt) of the experimental signal molecule composition (signal molecule+carrier). The Control seed was stored under the same conditions as the experimental seed prior to planting and planted at the same time as the experimental seed in the same soil. The results are shown in Table 3.

TABLE 3

| | Treatment | | | |
|---|---|---|---|---|
| | 1 month after treatment | | 1 yr after treatment | |
| | Root length (cm) | Root Vol. (cm³) | Root length (cm) | Root Vol. (cm³) |
| Control | 128 | 0.455 | 115.5 | 0.403 |
| LCO | 135* | 0.468 | 159.3* | 0.540* |
| % increase | 5.46 | 2.86 | 37.92 | 34 |

The results achieved by both inventive embodiments (seed treated with LCO at 1 month and 12 months prior to planting), and particularly the results obtained after the 1-year pretreatment, are dramatic, considering that it is known in the art that soybean seed are prone to deteriorate over that length of time.

Example 4

Figure 3:
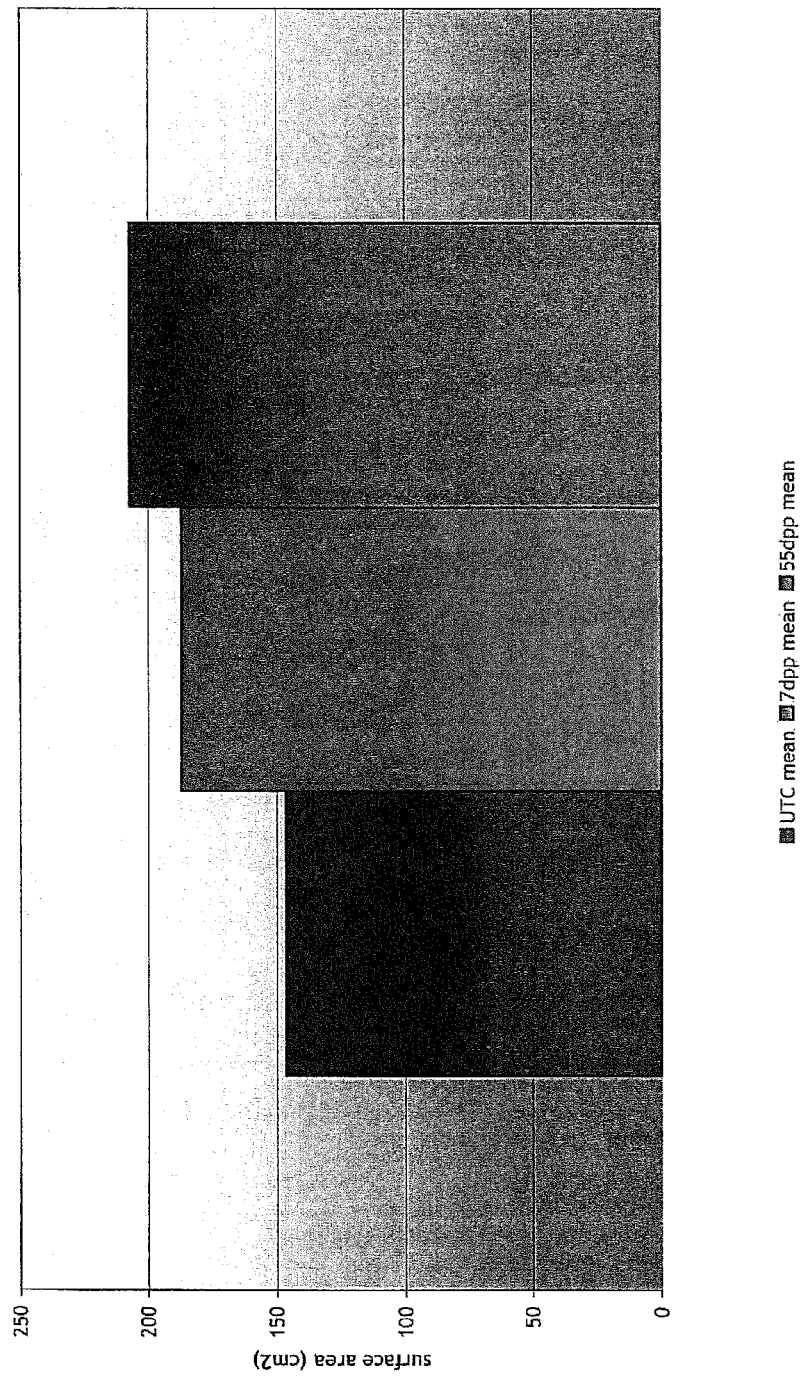
FIG. 3 is a bar graph that shows mean surface area of first-trifoliate leaves on 19-day old soybean plants germinated from seed treated in accordance with an embodiment of the present invention (e.g., 55 days pre-planting) as compared to controls (i.e., untreated seed and seed treated with the signal molecule 7 days prior to planting).

Soybean seeds treated with Optimize® were kept at 15° C. in a refrigerator. Seeds were planted 7 (7 dpp) and 55 (55 dpp) days after treatment in root boxes containing a peat:perlite mix. Their leaf surface area (cm²) were taken from the first trifoliate after 19 days. As illustrated in FIG. 3 and shown in Table 4, the leaves generated from seed treated in accordance with the present invention had a 50% greater mean increase in leaf surface area compared to the

TABLE 4

| | Mean | STDEV | Response | Response % |
|---|---|---|---|---|
| UTC mean | 146.25 | 18.7539 | | |
| 7 dpp mean | 187.05 | 29.8215 | 40.81 | 28% |
| 55 dpp mean | 207.18 | 20.5278 | 60.93 | 42% |

Since it is known that the bacterial (*Bradyrhizobium japonicum*) count on seed decreases over time, the increase in mean surface area shown in plants generated from seed treated 55 days prior to planting may be attributable to the rhizobial LCO.

All patent and non-patent publications cited in this specification are indicative of the level of skill of those skilled in the art to which this invention pertains. All these publications are herein incorporated by reference to the same extent as if each individual publication or patent application were specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of enhancing plant growth, comprising treating a seed at least one month prior to planting with an effective amount of a plant signal molecule, wherein the plant signal molecule is a lipo-chitooligosaccharide (LCO) and wherein, upon harvesting, the plant exhibits at least one of increased plant yield measured in terms of bushels/acre, increased root number, increased root length, increased root mass, increased root volume and increased leaf area, compared to plants harvested from control seeds treated with the plant signal molecule just prior to or within a week or less of planting.

2. The method of claim 1, wherein the LCO is synthetic.

3. The method of claim 1, wherein the LCO is recombinant.

4. The method of claim 1, wherein the LCO is naturally occurring.

5. The method of claim 1, wherein the plant signal molecule is applied in the form of a seed treatment composition comprising the plant signal molecule and an agriculturally acceptable carrier.

6. The method of claim 1, wherein the seed is leguminous.

7. The method of claim 6, wherein the leguminous seed is a soybean seed.

8. The method of claim 1, wherein the seed is non-leguminous.

9. The method of claim 8, wherein the non-leguminous seed is a field crop seed.

10. The method of claim 9, wherein the non-leguminous seed is a corn seed.

11. The method of claim 8, wherein the non-leguminous seed is a vegetable crop seed.

12. The method of claim 1, wherein the seed is treated with the plant signal molecule at least 9 months prior to planting.

13. The method of claim 1, wherein the seed is treated with the plant signal molecule at least 12 months prior to planting.

14. The method of claim 1, wherein the seed is treated with the plant signal molecule at least 2 years prior to planting.

15. The method of claim 1, wherein the LCO is isolated and/or purified from a species of *Rhizobia* selected from the group consisting of *Bradyrhizobium* spp., *Rhizobium* spp., *Sinorhizobium* spp. and *Azorhizobium* spp.

16. The method of claim 1, wherein the LCO is isolated and/or purified from *Bradyrhizobium japonicum*.

17. The method of claim 1, wherein the LCO is isolated and/or purified from an arbuscular mycorrhizal fungus.

18. The method of claim 1, further comprising contacting the seed with at least one phosphate solubilising microorganism.

19. The method of claim 1, further comprising contacting the seed with one or more strains of *Penicillium*.

20. The method of claim 1, further comprising contacting the seed with one or more strains of *P. bilaiae*.

21. The method of claim 1, further comprising contacting the seed with one or more strains of *P. gaestrivorus*.

22. The method of claim 1, further comprising contacting the seed with one or more strains of *Rhizobium*.

23. The method of claim 1, further comprising contacting the seed with one or more strains of *R. leguminosarum*.

24. The method of claim 1, further comprising contacting the seed with one or more strains of *Sinorhizobium*.

25. The method of claim 1, further comprising contacting the seed with one or more strains of *S. meliloti*.

26. The method of claim 1, further comprising contacting the seed with one or more strains of *Bradyrhizobium*.

27. The method of claim 1, further comprising contacting the seed with one or more strains of *B. japonicum*.

* * * * *